United States Patent
Wilson et al.

[19]

[11] Patent Number: 5,908,392
[45] Date of Patent: Jun. 1, 1999

[54] SYSTEM AND METHOD FOR RECORDING AND STORING MEDICAL DATA IN RESPONSE TO A PROGRAMMABLE TRIGGER

[75] Inventors: Raymond J. Wilson, Parker, Colo.; Laurence S. Sloman, West Hollywood, Calif.

[73] Assignee: Pacesetter, Inc., Sylmar, Calif.

[21] Appl. No.: 08/596,895

[22] Filed: Mar. 13, 1996

[51] Int. Cl.⁶ .................................................. A61B 5/0452
[52] U.S. Cl. .......................................... 600/509; 600/523
[58] Field of Search ................................... 600/509, 513, 600/515, 518, 516, 517, 519, 521, 522, 523; 607/2, 4, 5, 6, 9, 14, 17–26, 30, 62, 32

[56] References Cited

U.S. PATENT DOCUMENTS

| | | | |
|---|---|---|---|
| 4,250,888 | 2/1981 | Grosskopf | 600/515 |
| 4,295,474 | 10/1981 | Fischell | 600/509 |
| 4,966,157 | 10/1990 | Suzuki | 600/509 |
| 5,205,283 | 4/1993 | Olson | 600/518 |
| 5,513,645 | 5/1996 | Jacobson et al. | 600/518 |

*Primary Examiner*—William E. Kamm
*Assistant Examiner*—Kennedy J. Schaetzle

[57] ABSTRACT

The system of the present invention records and stores, in long-term memory and in form of data snapshots, medical data acquired prior to and subsequent to an occurrence of cardiac episodes and implantable device functions defined as important by the medical practitioner. The system provides the medical practitioner with the ability to specify trigger criteria representative of important cardiac episodes and implantable device functions. The system of the present invention allows the medical practitioner to control the amount of medical data stored in the data snapshots. The system allows the medical practitioner to specify a mode of storing data snapshots when the maximum storage capacity of long-term memory has been reached. In a first mode, the system stores data snapshots in a circular buffer manner, overwriting the older data snapshots. In a second mode, the system stops storing new data snapshots after the maximum storage capacity of long-term memory has been reached.

42 Claims, 11 Drawing Sheets

SYSTEM AND METHOD FOR RECORDING AND STORING MEDICAL DATA IN RESPONSE TO A PROGRAMMABLE TRIGGER

FIELD OF THE INVENTION

This invention relates to implantable medical devices, and in particular, to implantable medical devices that are capable of acquiring and storing medical data. More particularly, this invention relates to a system and method for recording and storing medical data, where the recording and storing of medical data is initiated by a programmable trigger.

BACKGROUND OF THE INVENTION

Some implantable medical devices, such as pacemakers, defibrillators, and cardioverters (collectively referred to as implantable cardiac stimulating devices) are designed to monitor and stimulate the cardiac tissue of patients who suffer from cardiac arrhythmias. Using leads connected to the patient's heart, a cardiac stimulating device typically stimulates cardiac tissue by delivering electrical pulses in response to measured cardiac events which are indicative of a cardiac arrhythmia. Properly administered therapeutic electrical pulses often successfully reestablish or maintain the heart's regular rhythm. Implantable cardiac stimulating devices can treat a wide range of cardiac arrhythmias by using a series of adjustable parameters to alter the energy content, the shape, the location, and the frequency of the therapeutic pulses. The adjustable parameters are usually stored in a memory of the implantable device. The adjustable parameters can be defined or altered telemetrically by a medical practitioner using an implantable device programmer, such as the one disclosed in the copending, commonly-assigned U.S. Pat. No. 5,724,985, issued Mar. 10, 1998, entitled "Improved User Interface for an Implantable Medical Device Using an Integrated Digitizer Display Screen", now U.S. Pat. No. 5,724,985, which is hereby incorporated by reference in its entirety.

After initial implantation and configuration of the implantable medical device, the medical practitioner typically performs periodic follow-up examinations to determine if the device is operating properly. On occasion, it may also be desirable for the medical practitioner to alter the device settings to improve the performance of the device. In order to make appropriate decisions regarding such changes, the medical practitioner should consider not only the current condition of the patient and the implantable medical device, but also historical information representative of changes to the patient's condition and changes in the operational characteristics of the implantable medical device.

Historical medical data should be taken into account because, while most implantable medical devices serve patients for years, certain physiologic and parametric changes having an impact on the performance of the device may occur during the time of service. These changes may include changes in characteristics of the patient's cardiac disorder, changes in the patient's course of drug therapy, changes in the patient's overall health, as well as changes in the operational characteristics of the implantable medical device (such as lead impedance and remaining battery life). In addition, medical knowledge about cardiac disorders and preferred methods of treatment may advance during the time of service.

Several approaches to gathering and presenting historical medical data have been developed to address the medical practitioners' needs. One such system for compiling and storing historical medical data measured by the medical practitioner during previous follow-up visits and medical data acquired between visits by the implantable device, is disclosed in the copending, commonly-assigned U.S. Pat. No. 5,722,999, issued Mar. 3, 1998, entitled "A System and Method for Storing and Displaying Historical. Medical Data Measured by an Implantable Medical Device", now U.S. Pat. No. 5,722,999, which is hereby incorporated by reference in its entirety.

While a significant amount of historical medical data is gathered during follow-up visits, often the most important events indicative of a patient's condition and the implantable device's performance occur between the follow-up visits. For example, most patients experience the majority of their cardiac arrhythmia episodes during the months between follow-up visits. In order to improve the medical practitioner's access to medical data representative of the patient's condition and of the performance of the implantable device, it was desirable to develop a technique for recording and storing medical data between follow-up visits.

In recent years, several approaches have been developed to enable implantable devices to record and store medical data between follow-up visits. The first approach to recording inter-visit medical data involves simply recording all medical data into the implantable device storage memory up to that memory's capacity. The second approach to recording inter-visit medical data, involves using a circular buffer to store the data. A circular buffer is a memory management scheme which stores a certain amount of data and discards a proportional amount of old data when a certain amount of new data is received. Thus, if a circular buffer has a capacity of storing twenty data items, the twenty first data item stored in the buffer would overwrite the first data item, and so on. Neither the direct memory storage approach, nor the circular buffer approach, provides the medical practitioner with the most important form of inter-visit medical data—medical data recorded during a cardiac episode (e.g., arrhythmia, a series of Premature Ventricular Contractions (PVCs)), and during the performance of an implantable device function (e.g., mode switching). Thus, it would be desirable to enable the implantable device to record and store inter-visit medical data recorded during a cardiac episode and during the performance of an implantable device function.

This need is partially addressed by a third approach to recording inter-visit medical data. The third approach to recording inter-visit medical data allows the patient to trigger recording of the data via some form of a remote control device linked to the implantable device. For example, if the patient is feeling uncomfortable, the patient may initiate the recording function so that at the next follow-up visit the medical practitioner may view and analyze the medical data recorded by the medical device during the incident of the patient's discomfort. However, this approach has a limitation in that the recording of the cardiac data is left to the patient's discretion and ability to trigger it.

Thus, it would be desirable for the medical practitioner to define what inter-visit medical data is important enough to be recorded and stored. It would also be desirable for the implantable device to automatically record and store inter-visit medical data which is defined as important by the medical practitioner. It would further be desirable to record inter-visit medical data both before and after an important cardiac episode is detected and before and after a performance of an implantable device function.

SUMMARY OF THE INVENTION

The disadvantages and limitations discussed above are overcome by the present invention. In accordance with this invention, a system and method are provided for automatically recording and storing inter-visit medical data, where a programmable trigger initiates the recording of medical data into long-term memory, and where the medical data acquired prior to the programmable trigger are stored in long-term memory.

The implantable device of the present invention includes a control system for controlling the operation of the implantable device, a set of leads for receiving atrial and ventricular signals and for delivering atrial and ventricular stimulation pulses, a set of amplifiers for amplifying the atrial and ventricular signals and waveforms, and pulse generators for generating atrial and ventricular stimulation pulses. In addition, the implantable device includes memory for storing operational parameters for the control system and for storing inter-visit data acquired by the control system for later retrieval by the medical practitioner using an external programmer. The implantable device also includes a telemetry circuit for communicating with the external programmer.

The memory of the implantable device of the present invention includes two temporary circular buffers—one for storing information indicative of cardiac events and another for storing cardiac waveform samples. The size of each temporary buffer is selected by the medical practitioner. The memory also stores a set of programmable trigger criteria selected by the medical practitioner via the external programmer from a list provided by the implantable device manufacturer. The trigger criteria define what cardiac episodes (e.g., various types of arrhythmias) and implantable device functions (e.g., automatic mode switching) the medical practitioner considers important enough to be recorded.

When the control system determines that one of the trigger criteria is met, the control system creates a data snapshot consisting of an event snapshot and a waveform snapshot. The event snapshot includes cardiac event data recorded before and after the trigger criterion has been met. Similarly, the waveform snapshot includes waveform data recorded before and after the trigger criterion has been met.

The implantable device memory also includes two separate snapshot buffers for long-term storage of event and waveform snapshots. During each program cycle the control system acquires data indicative of a cardiac event and one or more waveform samples from the implantable device and stores them in their respective temporary buffers. The control system then checks if any of the programmable trigger criteria have been met during the current program cycle. If at least one of the programmable trigger criteria has been met the control system creates a new event snapshot by transferring the contents of the temporary event buffer into an event snapshot buffer and by placing a mark in the event snapshot buffer indicating which trigger criterion initiated the formation of this event snapshot. The control system also places a time/date stamp. The control system also creates a new waveform snapshot by transferring the contents of the temporary waveform buffer into a waveform snapshot buffer and by placing a mark in the waveform snapshot buffer indicating which trigger criterion initiated the formation of this waveform snapshot. The control system also places a time/date stamp. The control system continues to record new cardiac events and waveform samples directly into the event and waveform snapshots, respectively, during future program cycles until a specified number of cardiac events or waveforms have been stored following the trigger mark. The control system continues its normal operation of recording cardiac events and waveforms into the temporary event and waveform buffers, respectively, and checking whether any trigger criteria are met.

Thus, unlike the previous approaches for recording inter-visit data, the implantable device of the present invention records only the data defined as important by the medical practitioner. Furthermore, cardiac data recorded prior to and subsequent to the important cardiac episode or implantable device function provides the medical practitioner with valuable information about the patient's condition and about the performance of the implantable device.

A medical practitioner may want to conserve the implantable device memory and resources by recording and storing only event snapshots, only waveform snapshots or to turn off snapshot recording entirely. Thus, the system of the present invention enables the medical practitioner to activate or deactivate one or both of the event and snapshot buffers.

Because of storage memory limitations in implantable devices, only a certain amount of data snapshots may be stored in the long-term memory. The system of the present invention enables the medical practitioner to select the size of the event and waveform snapshots, and thus to determine the maximum amount of event and waveform snapshots that may be stored in long-term memory. Furthermore, the medical practitioner is able to select a mode of snapshot recording. In a first mode of snapshot recording, after the maximum amount of snapshots have been stored, the snapshot buffers operate in a circular fashion and allow the next snapshot to overwrite the oldest snapshot stored in the buffer. In this manner, during a follow-up visit the medical practitioner is presented with the latest data snapshots. In a second mode of snapshot recording, after the maximum amount of snapshots have been stored, the snapshot buffers are deactivated and no further snapshots are recorded.

In this manner, during a follow-up visit the medical practitioner is presented with the earliest data snapshots.

The present invention improves the medical practitioner's decision-making ability with regard to appraising the performance of the implantable medical device and selecting a course of therapy, by providing the medical practitioner with cardiac data recorded prior to and subsequent to occurrences of cardiac episodes and implantable device functions defined by the medical practitioner as being important.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENT

Implantable cardiac stimulating devices are commonly used implantable medical devices and will be used to illustrate the principles of the present invention. It should be understood, however, that the principles of the present invention apply equally as well to other types of implantable medical devices, such as, rate-responsive pacemakers, anti-tachycardia pacemakers, cardioverters, defibrillators, and other devices which are intended to monitor a patient's physical condition.

Figure 1:
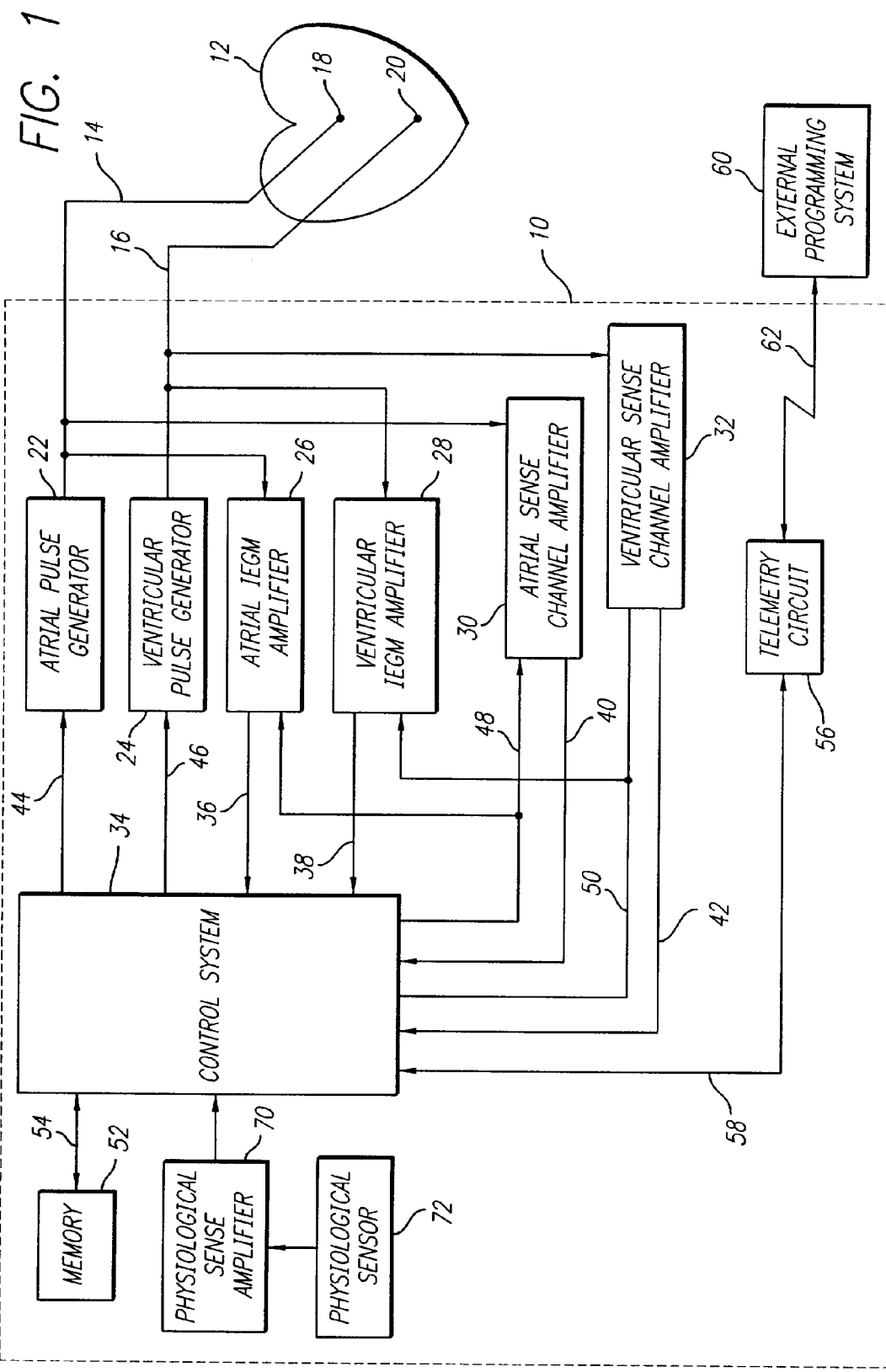
FIG. 1 is a schematic block diagram of a system for recording and storing inter-visit medical data, where the recording and storing of medical data is initiated by programmable trigger criteria in accordance with the principles of the present invention.

A pacemaker 10 in accordance with this invention is shown in FIG. 1. The pacemaker 10 is coupled to a heart 12 by way of leads 14 and 16, the lead 14 having an electrode 18 which is in contact with one of the atria of the heart 12, and the lead 16 having an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14 to the input terminal of an atrial sense amplifier 26. Electrical signals from the ventricles are carried from the electrode 20, through the lead 16 to the input terminal of a ventricular sense amplifier 28.

Controlling the dual chamber pacemaker 10 is a control system 34. The control system 34 is preferably a microprocessor-based system such as the one disclosed in commonly-assigned U.S. Pat. No. 4,940,052, issued Jul. 10, 1990, entitled "Microprocessor Controlled Rate-Responsive Pacemaker Having Automatic Rate Response Threshold Adjustment," which is hereby incorporated by reference in its entirety. The control system 34 may also be a state logic-based system such as the one disclosed in U.S. Pat. No. 4,944,298, issued Jul. 31, 1990, entitled "Atrial Rate Based Programmable Pacemaker with Automatic Mode Switching Means", which is hereby incorporated by reference. The control system 34 also includes a real-time clock (not shown) for providing timing for monitoring cardiac events and for timing the application of therapeutic pulses by the pulse generators 22 and 24.

The control system 34 receives the output signals from the atrial intracardiac electrogram (IEGM) amplifier 26 over a signal line 36. Similarly, the control system 34 receives the output signals from the ventricular IEGM amplifier 28 over a signal line 38. These output signals are generated continuously when an IEGM waveform is being sampled from the heart 12 by the control system 34.

The control system 34 also receives the output signals from the atrial sense channel amplifier 30 over a signal line 40. Similarly, the control system 34 receives the output signals from the ventricular sense channel amplifier 32 over a signal line 42. These output signals are generated each time that an atrial event (e.g., a P-wave) or a ventricular event (e.g., an R-wave) is sensed within the heart 12.

The control system 34 also generates an atrial trigger signal which is sent to the atrial pulse generator 22 over a signal line 44, and a ventricular trigger signal which is sent to the ventricular pulse generator 24 over a signal line 46. These trigger signals are generated each time that a stimulation pulse is to be generated by one of the pulse generators 22 or 24. The atrial stimulation pulse is referred to simply as the "A-pulse," and the ventricular stimulation pulse is referred to as the "V-pulse."

During the time that either an A-pulse or a V-pulse is being delivered to the heart 12, the corresponding atrial amplifiers 26 and 30 or the ventricular amplifiers 28 and 32 is typically disabled by way of a blanking signal presented to the appropriate amplifier from the control system 34 over a signal line 48 for the atrial amplifiers 26 and 30 or a signal line 50 for the ventricular amplifiers 28 and 32. This blanking action prevents the amplifiers 26, 28, 30 and 32 from becoming saturated with the relatively large stimulation pulses which are present at their input terminals during pacing pulse delivery. This blanking action also prevents residual electrical signals (known as "after-potentials") present in the muscle tissue as a result of the pacemaker stimulation from being interpreted as atrial or ventricular events.

As shown in FIG. 1, the pacemaker 10 also includes a memory circuit 52 which is coupled to the control system 34 through a suitable data bus 54. The memory circuit 52 allows certain control parameters used by the control system 34 in controlling the operation of the pacemaker 10 to be stored and programmably modified, as required, in order to customize the operation of the pacemaker 10 to suit the needs of a particular patient. In addition, inter-visit data recorded during the operation of the pacemaker 10 (e.g., various types of inter-visit data as described below) may be stored in the memory circuit 52 in temporary and long-term memory buffers.

A telemetry circuit 56 is further included in the pacemaker 10. The telemetry circuit 56 is connected to the control system 34 by way of a suitable command/data bus 58. In turn, the telemetry circuit 56 may be selectively coupled to an external programming device 60 by means of an appropriate communication link 62. The communication link 62 may be any suitable electromagnetic link such as an RF (radio frequency) channel.

Commands may be sent by the medical practitioner to the control system 34 from the external programmer 60 through the communication link 62. Similarly, through this communication link 62 and the external programmer 60, data (either held within the control system 34, as in a data latch, or stored within the memory circuit 52), may be remotely transmitted by the pacemaker 10 to the external programmer 60. In this manner, non-invasive communication may be established with the implanted pacemaker 10 from a remote, non-implanted location.

The control system 34 also may include a physiological sense amplifier 70 for receiving signals from a physiological sensor 72, which sensor may be included within the pacemaker 10 (as shown in FIG. 1) or within the lead system, 14 or 16 (not shown). Such sensors are well known in the art and may include one or more of: an activity sensor, an accelerometer, blood oxygen sensors, pH sensors, temperature sensors, QT interval measurements, gradient or evoked response measurements, pressure sensors, stroke volume or blood flow sensors, impedance sensors, minute ventilation sensors, etc.

The operation of the pacemaker 10 is generally controlled by a control program stored in the memory circuit 52 and executed by the control system 34. This control program usually consists of multiple integrated program modules, with each module bearing responsibility for controlling one or more functions of the pacemaker 10. For example, one program module may control the delivery of stimulating pulses to the heart 12, while another module may control the acquisition of atrial and ventricular electrical signals. In effect, each program module is a control program dedicated to a specific function or a set of functions of the pacemaker 10.

Before describing the operation of the control program in greater detail it is helpful to define the memory structure and representative variables used for temporary and long-term storage of inter-visit medical data by the pacemaker 10 in accordance with the present invention.

An EVENT is representative of a single cardiac event occurring within a cardiac cycle. Cardiac events include, but are not limited to P-waves, R-waves, A-pulses, V-pulses, and premature ventricular contractions (PVCs). The EVENT indicates that a particular cardiac event occurred, but it does not provide the morphology of the event. Under normal circumstances, several EVENTs occur during a cardiac cycle in a particular sequence. The time relationship between sequential EVENTs is represented by an EVENT_TIME which indicates the time between an EVENT and the previous EVENT in milliseconds. A sequence of EVENTs and EVENT_TIMEs provides a relatively accurate picture of cardiac activity over one or more cardiac cycles. A cardiac episode, such as an occurrence of tachycardia may be represented by a particular sequence of EVENTs and EVENT_TIMES. Furthermore, cardiac parameters such as the natural tissue refractory period may be derived from a collection of EVENTs and EVENT_TIMEs acquired during a single cardiac cycle.

The control system 34 continuously monitors cardiac activity through the atrial sense channel amplifier 30 and the ventricular sense channel amplifier 32. The control system 34 identifies EVENTs occurring during each cardiac cycle and also measures the EVENT_TIME between EVENTs. The EVENTs and EVENT_TIMEs are then stored in the memory circuit 52.

A SAMPLE is representative of a single digitized sample of cardiac waveform data sampled by the control system 34 through the atrial IEGM amplifier 26 or the ventricular IEGM amplifier 28. Examples of cardiac waveform data include, but are not limited to, atrial and ventricular intracardiac electrograms (IEGM) and raw sensor data representative of a patient's physical activity. A sequence of SAMPLEs provides a digital approximation of an analog waveform. A SAMPLING_RATE defines how many SAMPLEs of a particular waveform are acquired within a certain time. As a result, a high SAMPLING_RATE provides a better approximation of the waveform, since more SAMPLEs are available to reconstruct it.

The control system 34 continuously samples cardiac waveform data from a particular type of cardiac activity selected by the medical practitioner. The source of the selected cardiac activity is indicated by a WAVEFORM_SOURCE. The SAMPLEs representative of the sampled cardiac waveform are then stored in the memory circuit 52. A data compression scheme could be used to reduce the memory storage requirements and increase the recording time, as is known in the art.

Figure 2:
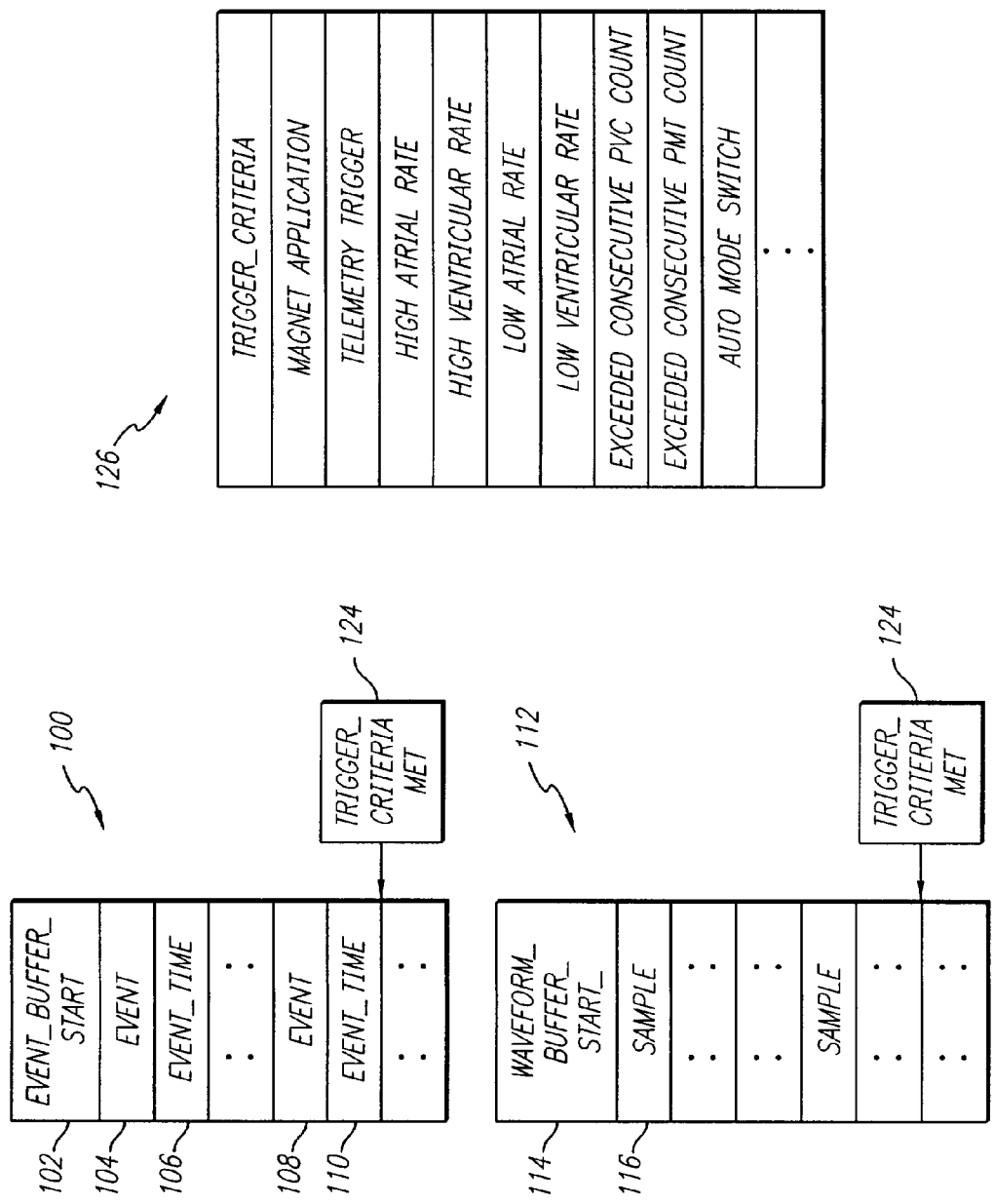
FIG. 2 depicts two data buffers for temporarily storing inter-visit medical data and a table which contains examples of programmable trigger criteria in accordance with the principles of the present invention.

In FIG. 2, two portions of the memory circuit 52 (FIG. 1) that are used for storing inter-visit medical data are shown. The first portion is a temporary event buffer 100 which is preferably used to store EVENTs and EVENT_TIMEs. The temporary event buffer 100 is preferably a circular buffer which sequentially stores a collection of EVENTs and EVENT_TIMEs identified and measured by the control system 34 (FIG. 1) respectively. A circular buffer is a memory management scheme which stores a certain amount of data and discards a proportional amount of old data when a certain amount of new data is received. The temporary event buffer 100 is initialized by placing a pointer at an EVENT_BUFFER_START 102 position. A pointer is a well-known program function which indicates a position in the buffer into which the control system 34 (FIG. 1) must load the next data item, such as an EVENT or an EVENT_TIME. After the data item is loaded the pointer is moved to the next position in the buffer. When a circular buffer reaches its maximum capacity, the pointer is reset to its initial position, thus allowing the old data in the buffer to be overwritten.

As EVENTs are identified, they are placed in sequential locations in the temporary event buffer 100 with measured EVENT_TIMEs between them. For example, EVENT 104 is the first EVENT identified after the temporary event buffer 100 is initialized. EVENT_TIME 106 is the time measured between EVENT 104 and the next EVENT (not shown). When the maximum EVENT capacity for the temporary event buffer 100 is reached, the pointer is reset to the EVENT_BUFFER_START 102 (this operation is described in greater detail below in connection with FIGS. 5–11).

The maximum capacity of the temporary event buffer 100 is defined by a programmable variable EVENT_LIMIT_2 which indicates the maximum amount of EVENTs that may be stored in the temporary event buffer 100 without overwriting the first EVENT in the buffer.

The second portion of the memory circuit 52, is a temporary waveform buffer 112 which is preferably used to store SAMPLEs. The temporary waveform buffer 112 is a circular buffer which sequentially stores a collection of SAMPLEs representative of a particular cardiac waveform sampled by the control system 34 (FIG. 1). The temporary waveform buffer 112 is initialized by placing a pointer at a WAVEFORM_BUFFER_START 114 position. As a cardiac waveform is sampled, SAMPLEs are placed sequentially into the temporary waveform buffer 112. For example, a SAMPLE 116 is the first SAMPLE acquired after initialization. When the maximum SAMPLE capacity for the temporary waveform buffer 112 is reached, the pointer is reset to the WAVEFORM_BUFFER_START 114. The maximum capacity of the temporary waveform buffer 112 is defined by a programmable variable SAMPLE_LIMIT_1 which indicates the maximum amount of SAMPLEs that may be stored in the temporary waveform buffer 112 without overwriting the first SAMPLE in the buffer.

Both the temporary event buffer 100 and the temporary waveform buffer 112 are similar to previous approaches in that they store inter-visit medical data without reference to the data's importance to the medical practitioner. In addition, the circular buffer data storage scheme used by both buffers continuously overwrites old data. As a result, important inter-visit data representative of a cardiac episode of interest to the medical practitioner may be quickly lost as the old data is overwritten. The present invention provides a solution to this problem by storing, in long-term memory, collections of EVENTs and waveform SAMPLEs that describe the patient's cardiac activity prior to and after particular cardiac episodes and occurrences of pacemaker functions which are defined as important by the medical practitioner.

A set of TRIGGER_CRITERIA is representative of individual cardiac events and sequences of cardiac events which identify cardiac episodes that the medical practitioner considers important.

TRIGGER_CRITERIA are also representative of program flags indicating occurrences of important pacemaker functions. A TRIGGER_CRITERIA being met is shown in FIG. 2 as a pointer 124 and is described in greater detail below in connection with FIG. 3.

TRIGGER_CRITERIA are preferably selected by the medical practitioner from a list provided by the pacemaker manufacturer. A table 126 shows examples of typical TRIGGER_CRITERIA. The first TRIGGER_CRITERION, "magnet application," involves applying a magnet to the pacemaker 10 (FIG. 1) during a follow-up visit, which enables the medical practitioner to test the TRIGGER_CRITERIA initiated recording and storage of medical data. The second criterion, "telemetry trigger," allows the medical practitioner to remotely trigger recording and storage of medical data through telemetry. For example, if the patient has a telemetry-modem interface, the medical practitioner can trigger the recording and storage of medical data via a modem from a hospital computer or the implantable device programmer.

The third and fourth criteria, "high atrial rate" and "high ventricular rate," trigger recording and storage of medical data when the intrinsic atrial or ventricular rate, respectively, exceeds a pre-determined amount (typically 90–200 bpm). Similarly, the fifth and sixth criteria, "low atrial rate" and "low ventricular rate" trigger the recording and storage of medical data when the intrinsic atrial or ventricular rate, respectively, fall below a pre-determined amount (typically 50 bpm).

The seventh criterion "exceeded consecutive premature ventricular contraction (PVC) count," serves as a trigger when the control system 34 (FIG. 1) detects a pre-determined amount (typically 1–15) of consecutive occurrences of PVC. Similarly, the eighth criterion, "exceeded consecutive pacemaker-mediated tachycardia (PMT) count," serves as a trigger when the control system 34 (FIG. 1) detects a pre-determined amount (typically 1–15) of consecutive occurrences of PMT. The ninth criteria, "auto mode switch," initiates the storage and recording of medical data when the control system 34 (FIG. 1) causes the pacemaker 10 (FIG. 1) to switch pacing modes. For example, if the pacemaker 10 (FIG. 1) switches from an atrial-tracking mode (e.g., DDDR) to a non-atrial-tracking mode (e.g., VVIR) the recording and storage of medical data would be initiated.

The TRIGGER_CRITERIA are not limited to the above-described examples and may include two or more criteria combined using Boolean operators. For example, a TRIGGER_CRITERION may be "high atrial rate AND exceeded consecutive pacemaker-mediated tachycardia (PMT) count," in which case both of the criteria must be met before the recording and storage of medical data is initiated.

Figure 3:
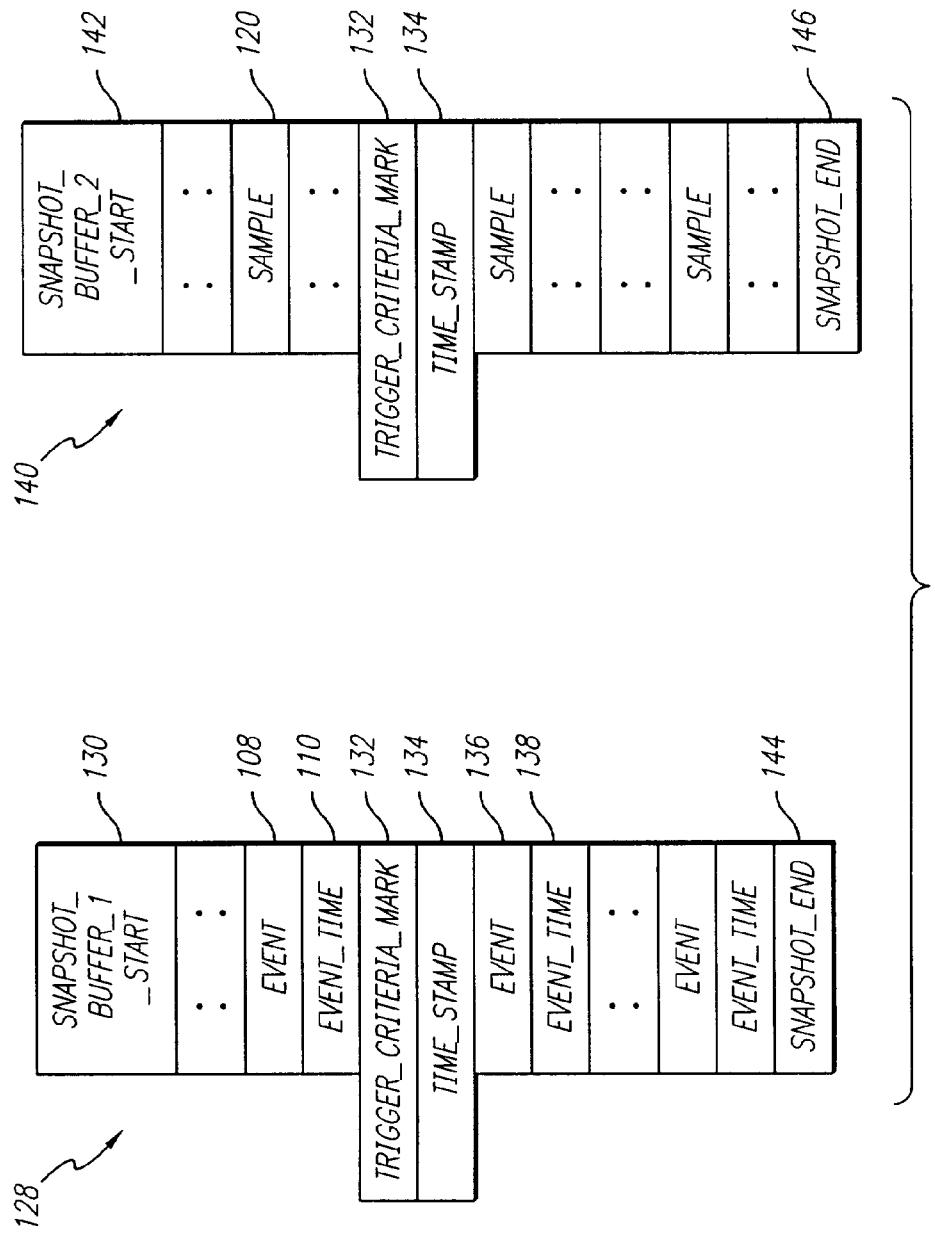
FIG. 3 depicts two data buffers for long-term storage of inter-visit medical data in accordance with the principles of the present invention.

In FIG. 3, two portions of the memory circuit 52 that are used for long-term storage of inter-visit medical data are shown. When one of the TRIGGER_CRITERIA is met, as indicated by the pointer 124 (FIG. 2) the formation of a data snapshot by the control system 34 (FIG. 1) is initiated. A data snapshot consists of an event snapshot and a waveform snapshot. The event snapshot is a collection of EVENTs and EVENT_TIMEs recorded prior to and subsequent to the same TRIGGER_CRITERIA being met. Similarly, the waveform snapshot is a collection of SAMPLEs recorded prior to and subsequent to one of the TRIGGER_CRITERIA being met. Each of the event and waveform snapshots also contains a TRIGGER_CRITERION_MARK which indicates the particular TRIGGER_CRITERION responsible for initiating the formation of that event and waveform snapshot. The TRIGGER_CRITERION_MARK is followed by a TIME_STAMP which indicates the time and date at which the TRIGGER_CRITERION_MARK was placed into the event and waveform snapshots. Event snapshots are stored in an event snapshot buffer 128, while waveform snapshots are stored in a waveform snapshot buffer 140.

The initial position of an event snapshot buffer pointer is indicated by a SNAPSHOT_BUFFER_1_START 130, while the initial position of a waveform snapshot buffer pointer is indicated by a SNAPSHOT_BUFFER_2_START 142.

In summary, when a TRIGGER_CRITERION is met, as indicated by the pointer 124 (FIG. 2), the control system 34 (FIG. 1) transfers the contents of the temporary event buffer 100 (FIG. 2) into the event snapshot buffer 128. A TRIGGER_CRITERION_MARK 132 and a TIME_STAMP 134 are placed into the event snapshot buffer 128. The control system 34 (FIG. 1) then begins recording EVENTs and EVENT_TIMEs directly into the event snapshot buffer 128. The direct recording into the event snapshot buffer 128 is shown by an EVENT 136 and EVENT_TIME 138. The number of EVENTs that may be recorded into the event snapshot buffer 128 before normal operation is resumed, is defined by a programmable variable EVENT_LIMIT_1. When EVENT_LIMIT_1 EVENTs have been recorded, the control system 34 (FIG. 1) places a marker to signify the end of the event snapshot. The marker is shown as SNAPSHOT_END_1 144. The control system 34 (FIG. 1) then returns to the recording EVENTs and EVENT_TIMEs into the temporary event buffer 100 (FIG. 2).

Thus, an event snapshot consists of a collection of EVENTs and EVENT_TIMEs acquired prior to and subsequent to the TRIGGER_CRITERIA being met.

In response to the TRIGGER_CRITERION being met, the control system 34 (FIG. 1) also transfers the contents of the temporary waveform buffer 100 (FIG. 2) into the waveform snapshot buffer 140. The TRIGGER_CRITERIA_MARK 132 and a TIME_STAMP 134 are placed into the waveform snapshot buffer 140. The control system 34 (FIG. 1) then begins recording SAMPLEs directly into the waveform snapshot buffer 140. The number of SAMPLEs that may be recorded into the waveform snapshot buffer 140 is defined by a programmable variable SAMPLE_LIMIT_1. When SAMPLE_LIMIT_1 SAMPLEs have been recorded, the control system 34 (FIG. 1) places the SNAPSHOT_END_2 146 marker before returning to the normal operation of recording SAMPLEs into the temporary waveform buffer 112 (FIG. 2). Thus, a waveform snapshot consists of a collection of SAMPLEs acquired prior to and subsequent to the TRIGGER_CRITERIA being met.

In this manner, the medical practitioner is presented with detailed information of the patient's condition before and after an important cardiac episode (e.g., an arrhythmia) or a performance of an important pacemaker function (e.g., a mode switch).

A summary of the variables and data structures discussed above in connection with FIGS. 2–3 are shown in Tables 1 and 2, respectively.

TABLE 1

| Variable | Definition |
|---|---|
| EVENT | An indicator that a particular cardiac event has occurred (Example: a P-Wave). |
| EVENT_TIME | The time measured between the EVENT acquired during the current program cycle and the EVENT acquired during the previous program cycle. |
| EVENT_BUFFER_START | The initial position of the temporary event buffer pointer. |
| SAMPLE | A single digital sample of cardiac waveform data. A collection of samples is representative of a digital approximation of a waveform. |
| WAVEFORM_BUFFER_START | The initial position of the temporary waveform buffer pointer. |
| TRIGGER_CRITERIA | A set of programmable criteria, where if at least one of the criteria is met: (a) the transfer of the contents of the temporary event and waveform buffers to the event and waveform snapshot buffers, respectively, is initiated, and (b) the recording of EVENTs and SAMPLEs directly into the event and waveform snapshot buffers respectively, is triggered. |
| event snapshot | A collection of EVENTs and EVENT_TIMEs recorded prior to and after one of the TRIGGER_CRITERIA has been met. |
| SNAPSHOT_BUFFER_1_START | The initial position of the event snapshot buffer pointer. |
| TRIGGER_CRITERIA_MARK | An indicator in both the event and waveform snapshot buffers that one or more of the TRIGGER_CRITERIA have been met. |
| TIME_STAMP | An indicator of the time and date at which the TRIGGER_CRITERIA_MARK was placed into the event and waveform snapshot buffers. |
| waveform snapshot | A collection of waveform SAMPLEs recorded prior to and after one of the TRIGGER_CRITERIA has been met. |
| data snapshot | A data item consisting an event snapshot and a waveform snapshot. |
| SNAPSHOT_BUFFER_2_START | The initial position of the waveform snapshot buffer pointer. |
| WAVEFORM_SOURCE | A selectable source for the recording of SAMPLES (e.g., atrium, ventricles, etc.) |
| SAMPLE_LIMIT_1 | The maximum amount of SAMPLEs that may be stored in the temporary waveform buffer without overwriting the first SAMPLE in the buffer. |
| SAMPLE_LIMIT_2 | The maximum amount of SAMPLEs that may be stored in the waveform snapshot buffer after the TRIGGER_CRITERIA_MARK is placed. |
| SAMPLING_RATE | An indicator of how many SAMPLEs are acquired from the WAVEFORM_SOURCE in one program cycle. |
| EVENT_LIMIT 1 | The maximum amount of EVENTs that may be stored in the temporary event buffer without overwriting the first EVENT in the buffer. |
| EVENT_LIMIT_2 | The maximum amount of EVENTs that may be stored in the event snapshot buffer after the TRIGGER_CRITERIA_MARK is placed. |

TABLE 2

| Data Structure | Definition |
|---|---|
| temporary event buffer | A circular buffer for storing EVENTs and EVENT_TIMES. |
| temporary waveform buffer | A circular buffer for storing SAMPLEs. |
| event snapshot buffer | A memory area for storing event snapshots. |
| waveform snapshot buffer | A memory area for storing waveform snapshots. |

Figure 4:
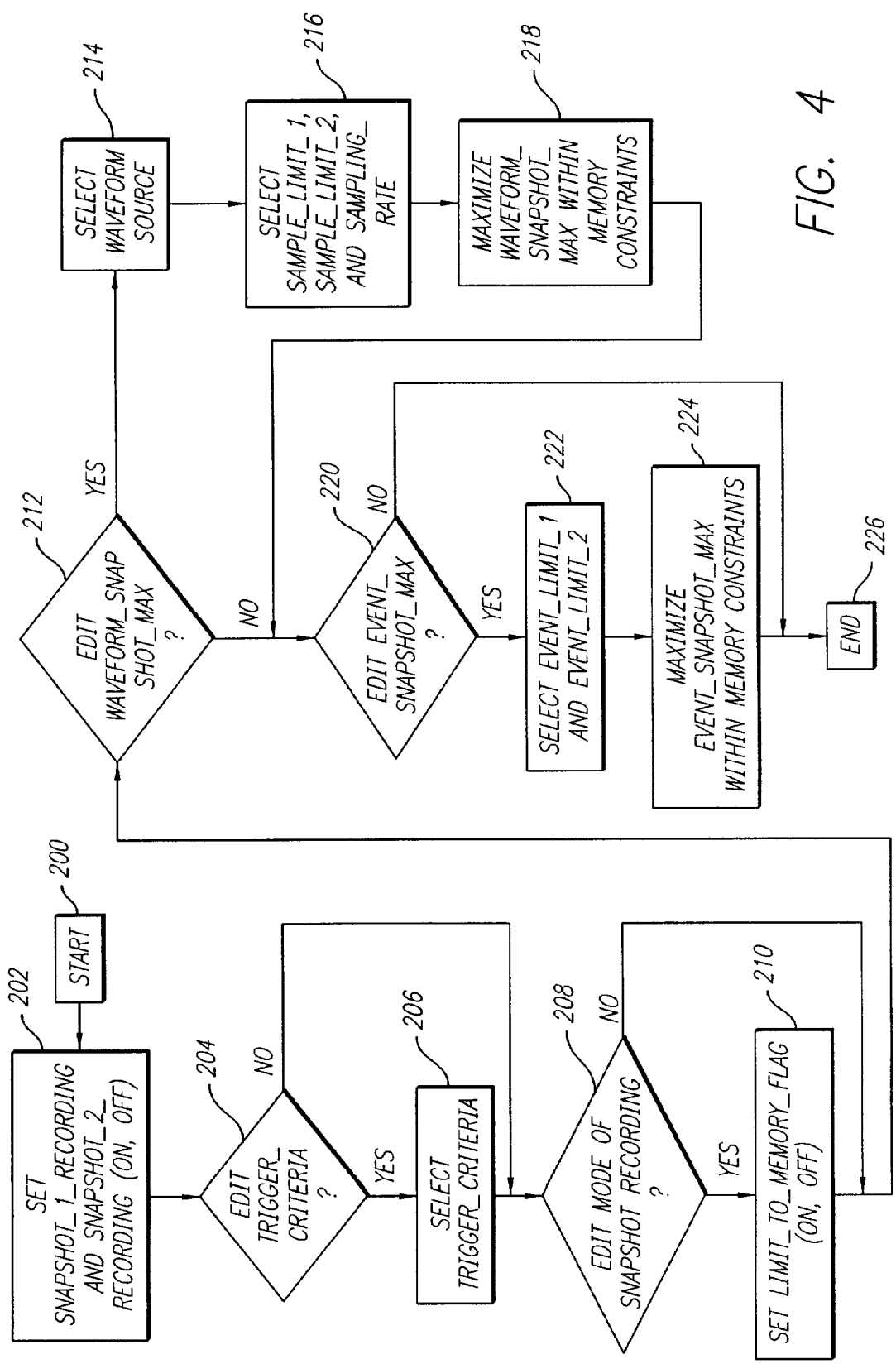
FIG. 4 depicts a logic flow diagram representative of a set-up program executed by an external programmer which is used to configure the system of FIG. 1 in accordance with the principles of the present invention.
Figure 5:
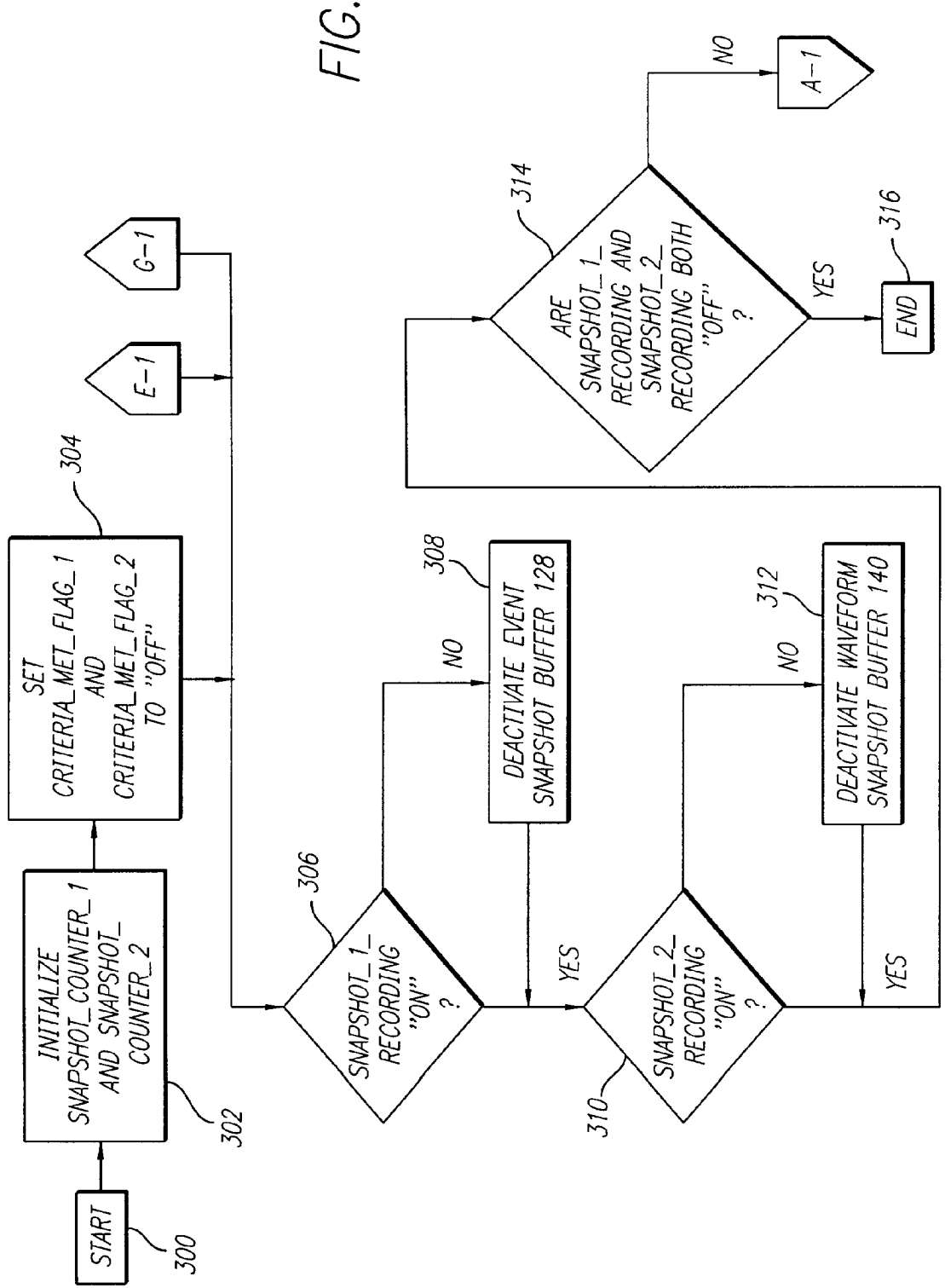
FIGS. 5–11 depict a logic flow diagram representative of a control program executed by the implantable device control unit which is used to record and store inter-visit medical data, where the recording and storing of medical data are initiated by the programmable trigger criteria in accordance with the principles of the present invention.
Figure 6:
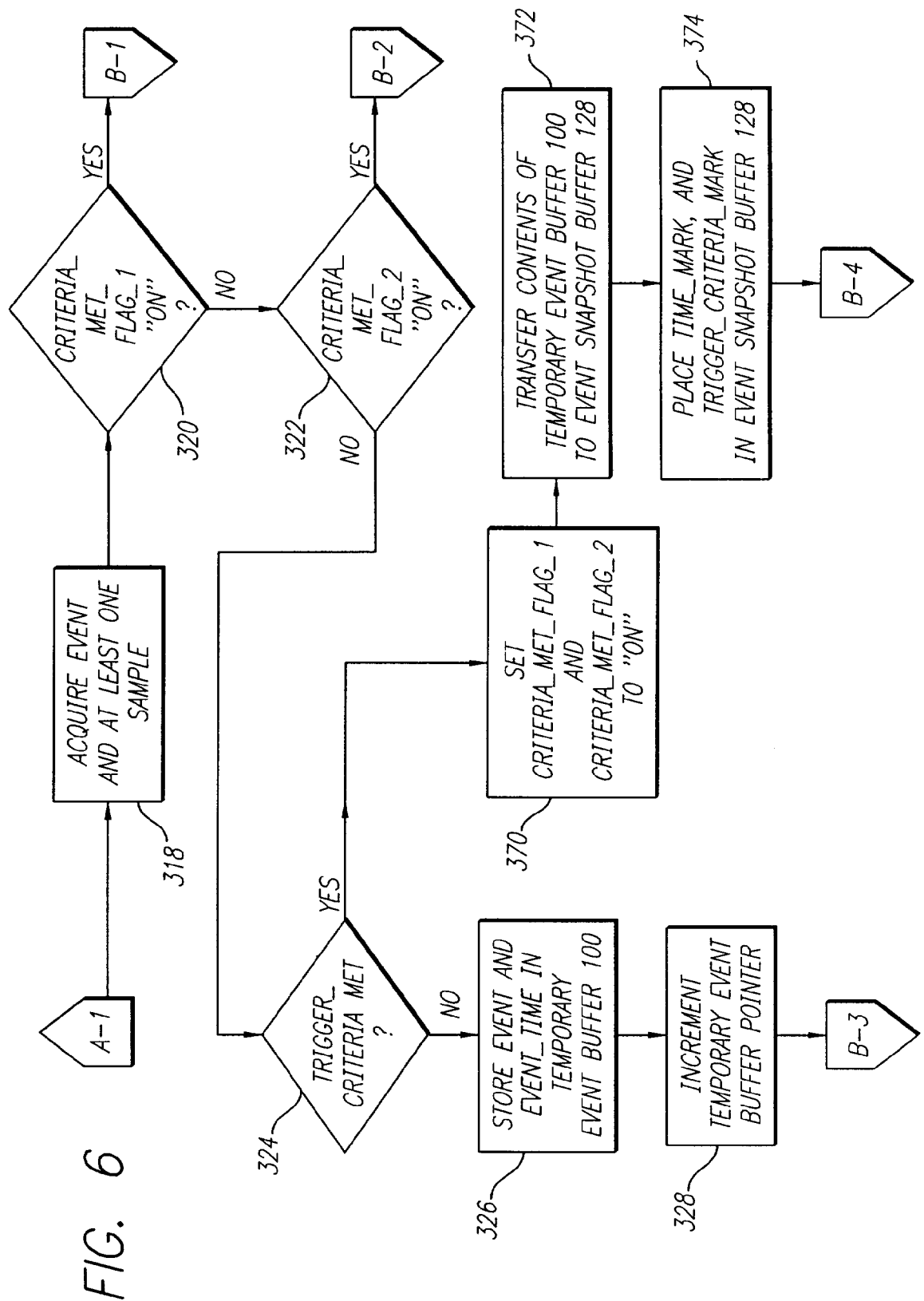
Figure 7:
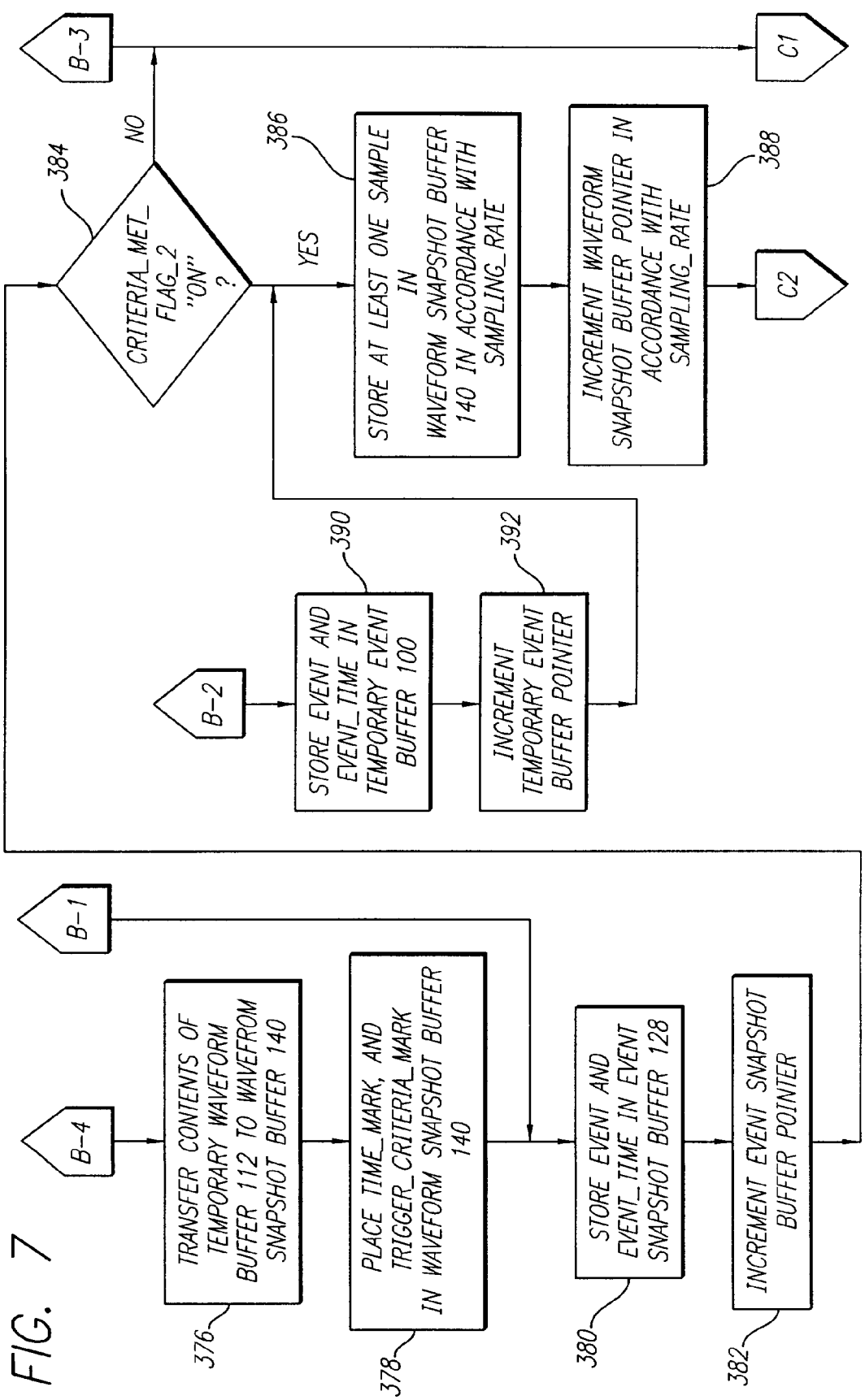
Figure 8:
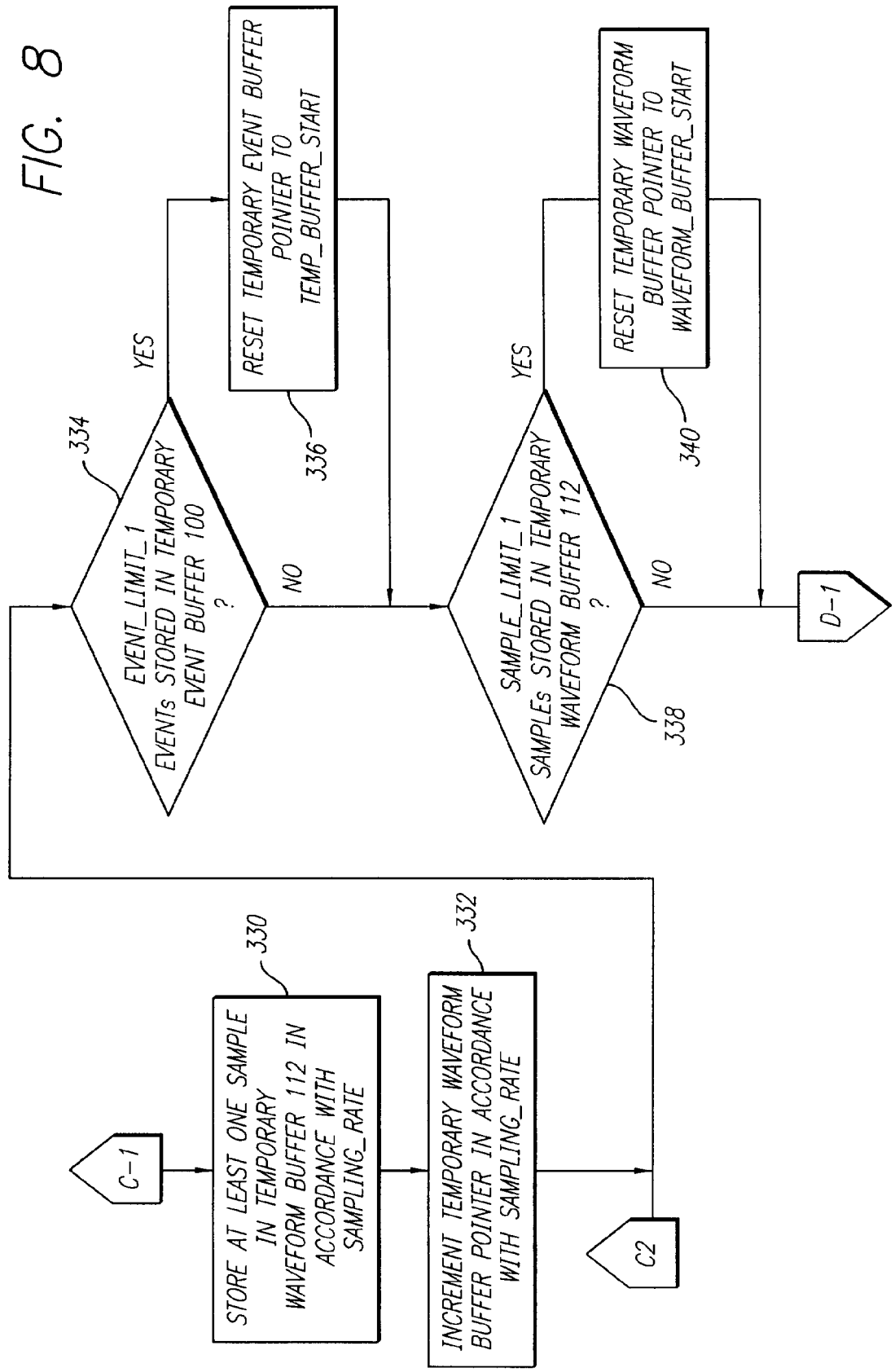
Figure 9:
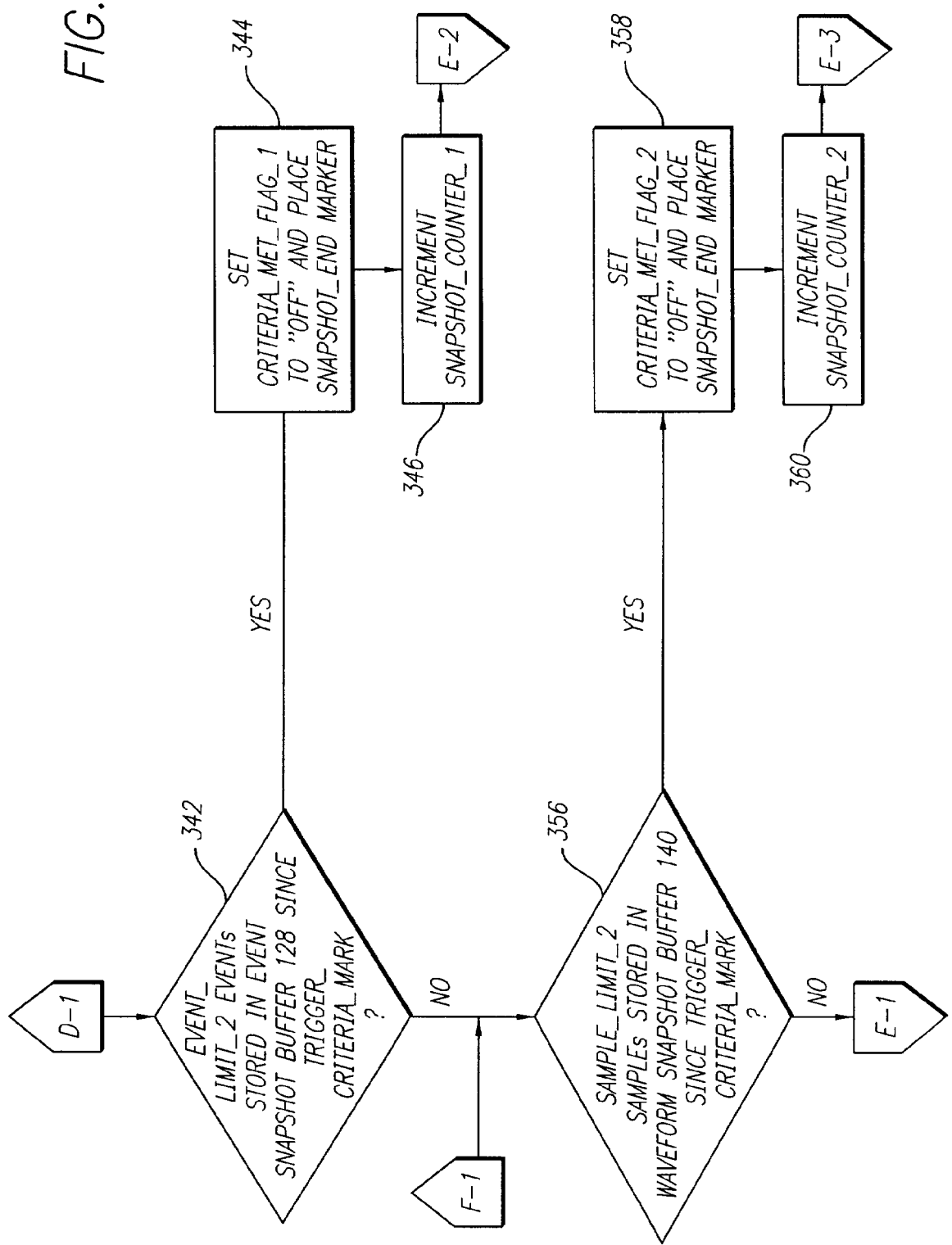
Figure 10:
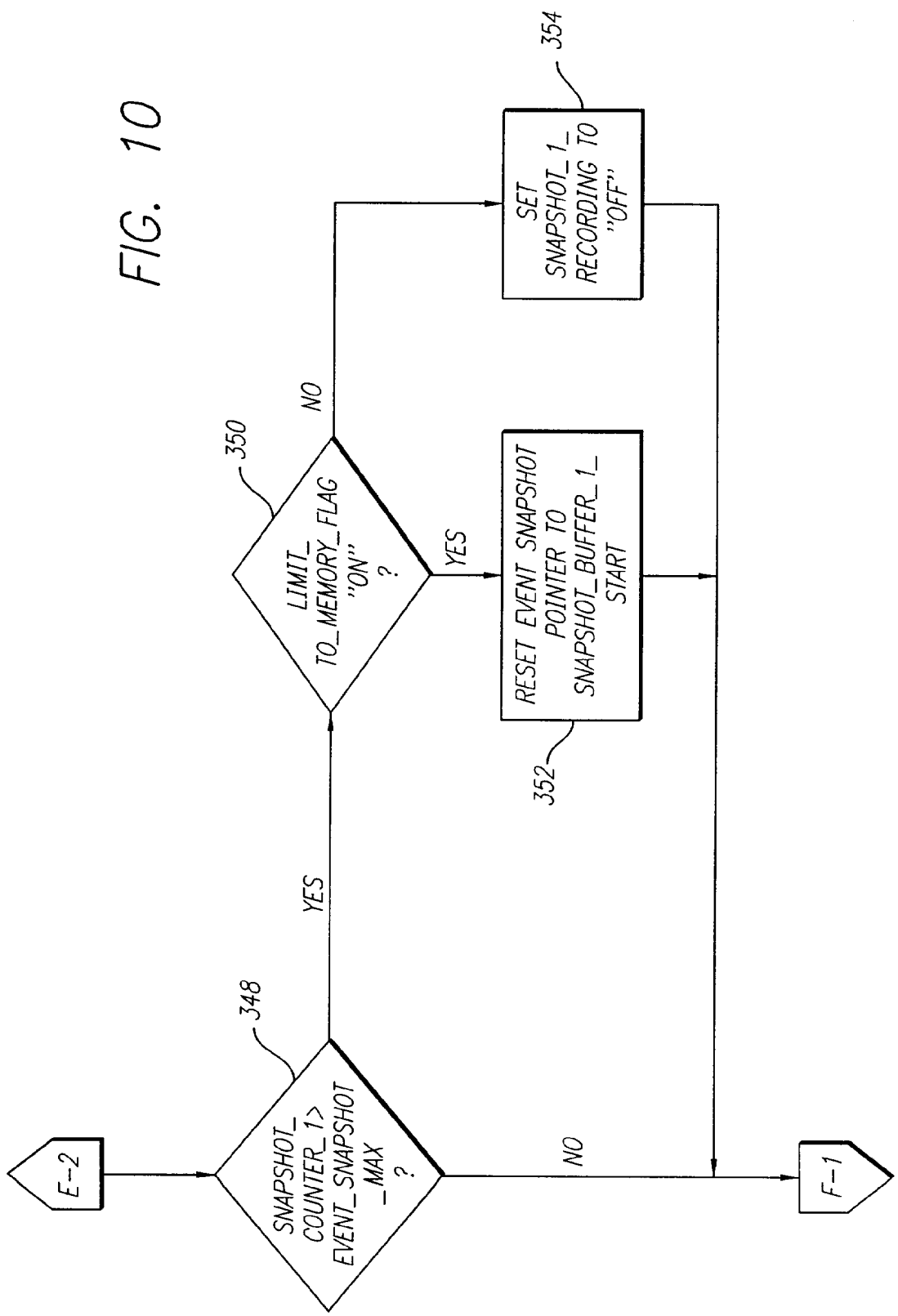
Figure 11:
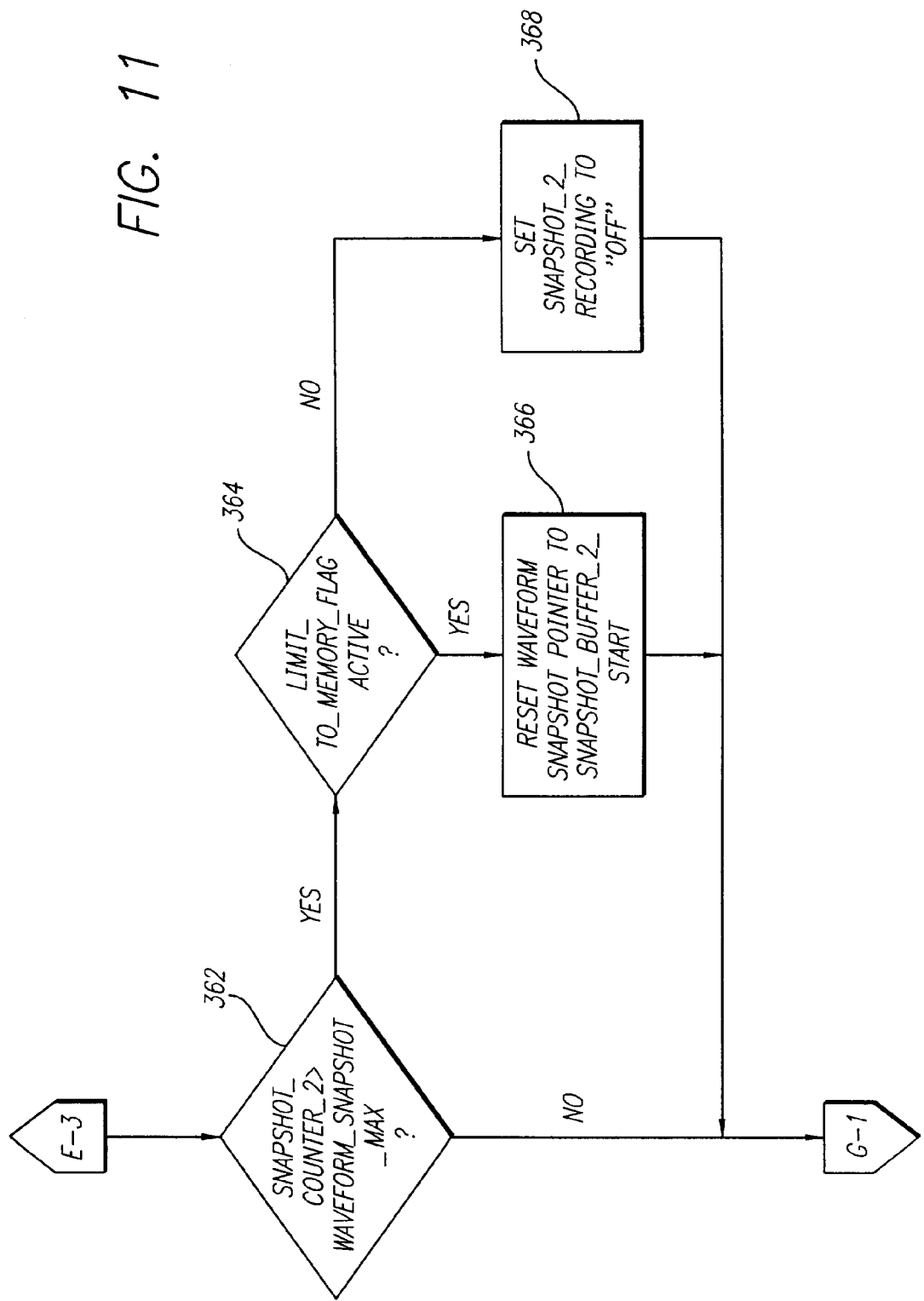

In FIG. 4, a logic flow diagram representing a set-up program for the control unit 52 of FIG. 1 in accordance with a preferred embodiment of the present invention is described. The set-up program may be used by the medical practitioner to select various parameters and set parameter values for a control program described below in connection with FIGS. 5–11. The set-up program is typically executed by the external programmer 60 (FIG. 1) during a follow-up visit. The external programmer 60 (FIG. 1) may communicate with the pacemaker 10 (FIG. 1) via the communication link 62 (FIG. 1).

After the medical practitioner begins the program at a step 200, the external programmer 60 (FIG. 1) prompts the medical practitioner to select whether SNAPSHOT_1_RECORDING and SNAPSHOT_2_RECORDING should be "ON" or "OFF," respectively. SNAPSHOT_1_RECORDING is a flag indicating whether event snapshots should be recorded by the control system. Similarly, SNAPSHOT_2_RECORDING is a flag indicating whether waveform snapshots should be recorded by the control system.

At a test 204, the external programmer 60 (FIG. 1) prompts the medical practitioner to indicate whether the set of TRIGGER_CRITERIA should be edited. If the TRIGGER_CRITERIA are to be edited, the external programmer 60 (FIG. 1) proceeds to a step 206, where a set of TRIGGER_CRITERIA may be selected from a list of TRIGGER_CRITERIA pre-defined by the manufacturer.

Optionally, the medical practitioner may define TRIGGER_CRITERIA which are unique to a particular patient by logically (i.e. by the AND, and OR operators) combining one or more TRIGGER_CRITERIA from the set into a single TRIGGER_CRITERA.

At a test 208, the external programmer 60 (FIG. 1) prompts the medical practitioner to indicate whether the mode of event snapshot recording should be edited. The mode of snapshot recording is indicated by a LIMIT_TO_MEMORY_FLAG. LIMIT_TO_MEMORY_FLAG is a flag indicating whether the most recent or the oldest data snapshots should be recorded. If "ON," this flag indicates that when the capacity of the event snapshot buffer 128 (FIG. 3) or the waveform snapshot buffer 140 (FIG. 3) is exceeded, new snapshots in the snapshot buffer with exceeded capacity should overwrite the previously recorded ones. If "OFF," this flag indicates that when the capacity of a snapshot buffer is exceeded further recording to that snapshot buffer should stop. If the mode of snapshot recording should be edited, the external programmer 60 (FIG. 1) prompts the medical practitioner to set the LIMIT_TO_MEMORY_FLAG at a step 210.

Even with the advances in pacemaker memory technology, the storage capacity of pacemaker memory is somewhat limited. As a result, only a certain number of event and waveform snapshots may be stored in the event and waveform buffers 128 and 140 (FIG. 3), respectively. At a test 212, the external programmer 60 (FIG. 1) prompts the medical practitioner to indicate whether WAVEFORM_SNAPSHOT_MAX should be edited. WAVEFORM_SNAPSHOT_MAX indicates a maximum number of waveform snapshots that may be stored in the waveform snapshot buffer 140 (FIG. 3).

If WAVEFORM_SNAPSHOT_MAX is to be edited, at a step 214 the medical practitioner selects the WAVEFORM_SOURCE which determines the type and the source of a waveform to be sampled by the control system 34 (FIG. 1). At a step 216, the medical practitioner selects values for the SAMPLE_LIMIT_1 and SAMPLE_LIMIT_2 variables, which define the size of each waveform snapshot, and also selects the SAMPLING_RATE.

At a step 218, the external programmer 60 (FIG. 1) calculates a maximum value for WAVEFORM_SNAPSHOT_MAX based on the values of SAMPLE_LIMIT_1 and SAMPLE_LIMIT_2 selected by the medical practitioner at the step 216.

The value of WAVEFORM_SNAPSHOT_MAX is inversely proportional to the values of SAMPLE_LIMIT_1 and SAMPLE_LIMIT_2. For example, if the medical practitioner wanted a larger waveform snapshot, the values of SAMPLE_LIMIT_1 and SAMPLE_LIMIT_2 would be set high. However, less waveform snapshots would be able to fit into the waveform snapshot buffer, and as a result WAVEFORM_SNAPSHOT_MAX would be lower.

At a test 220, the external programmer 60 (FIG. 1) prompts the medical practitioner to indicate whether EVENT_SNAPSHOT_MAX should be edited. EVENT_SNAPSHOT_MAX indicates a maximum number of event snapshots that may be stored in the event snapshot buffer 128 (FIG. 3). If EVENT_SNAPSHOT_MAX is to be edited, at a step 222 the medical practitioner selects values for the EVENT_LIMIT_2 and EVENT_LIMIT_1 variables. At a step 224, the external programmer 60 (FIG. 1) calculates a maximum value for EVENT_SNAPSHOT_MAX based on the values of EVENT_LIMIT_2 and EVENT_LIMIT_1 selected by the medical practitioner at the step 222. The external programmer 60 (FIG. 1) then proceeds to a step 226 where the set-up program ends.

As shown in FIGS. 5–11, a logic flow diagram representing a control program for the control system 34 of FIG. 1 in accordance with a preferred embodiment of the present invention is described. After the medical practitioner begins the program at a step 300, the control system 34 (FIG. 1) initializes SNAPSHOT_COUNTER_1 and SNAPSHOT_COUNTER_2 to "0" at a step 302. SNAPSHOT_COUNTER_1 is an indicator of how many event snapshots are currently stored in the event snapshot buffer 128 (FIG. 3). Similarly, SNAPSHOT_COUNTER_2 is an indicator of how many waveform snapshots are currently stored in the waveform snapshot buffer 140 (FIG. 3).

At a step 304, the control system 34 (FIG. 1) sets CRITERIA_MET_FLAG_1 and CRITERIA_MET_FLAG_2 to "OFF." CRITERIA_MET_FLAG_1 is a flag, which when "OFF," indicates that an EVENT acquired during the current program cycle should be placed into the temporary event buffer 100 (FIG. 2). When "ON," it indicates that an EVENT acquired during the current program cycle should be placed into the event snapshot buffer 128 (FIG. 3) instead of the temporary event buffer 100 (FIG. 2). Similarly, CRITERIA_MET_FLAG_2, is a flag which when "OFF," indicates that a SAMPLE acquired during the current program cycle should be placed into the temporary waveform buffer 112 (FIG. 2). When "ON," it indicates that a SAMPLE acquired during the current program cycle should be placed into the waveform snapshot buffer 140 (FIG. 3) instead of the temporary waveform buffer 112 (FIG. 2). At a test 306, the control system 34 (FIG. 1) determines whether SNAPSHOT_1_RECORDING is set to "ON." If SNAPSHOT_1_RECORDING is not set to "ON," the control system 34 (FIG. 1) proceeds to a step 308. At the step 308, the control system 34 (FIG. 1) deactivates the event snapshot buffer 128 (FIG. 3).

At a test 310, the control system 34 (FIG. 1) determines whether SNAPSHOT_2_RECORDING is set to "ON." If SNAPSHOT_2_RECORDING is not set to "ON," the control system 34 (FIG. 1) proceeds to a step 312. At the step 312, the control system 34 (FIG. 1) deactivates the waveform snapshot buffer 140 (FIG. 3).

At a test 314, the control system 34 (FIG. 1) determines whether SNAPSHOT_1_RECORDING and SNAPSHOT_2_RECORDING are both set to "OFF." If SNAPSHOT_1_RECORDING and SNAPSHOT_2_RECORDING are both set to "OFF," the control system 34 (FIG. 1) proceeds to a step 316 where it ends the control program. Otherwise, the control system 34 (FIG. 1) proceeds to a step 318. At the step 318, the control system 34 (FIG. 1) acquires an EVENT and a particular number of SAMPLEs in accordance with the SAMPLING_RATE via the leads 14 and 16 (FIG. 1).

At the test 320, the control system 34 (FIG. 1) determines whether the CRITERA_MET_FLAG_1 is set to "ON." This test determines to which buffer the EVENT acquired during the current program cycle should be recorded. If the CRITERA_MET_FLAG_1 is set to "ON," the control system 34 (FIG. 1) proceeds to a step 380. Otherwise, the control system 34 (FIG. 1) proceeds to a test 322. At the test 322, the control system 34 (FIG. 1) determines whether the CRITERA_MET_FLAG_2 is set to "ON." This test determines to which buffer the SAMPLEs acquired during the current program cycle should be recorded. If the CRITERA_MET_FLAG_2 is set to "ON," the control system 34 (FIG. 1) proceeds to a step 390. Otherwise, the control system 34 (FIG. 1) proceeds to a test 324.

At the test 324, the control system 34 (FIG. 1) determines whether one of the TRIGGER_CRITERIA has been met during the current program cycle. Examples of TRIGGER_CRITERIA are shown in the table 126 (FIG. 2). If none of the TRIGGER_CRITERIA have been met, the control system 34 (FIG. 1) proceeds to a step 326. At the step 326, the control system 34 (FIG. 1) measures the EVENT_TIME from the EVENT acquired during the previous program cycle, and then stores the EVENT acquired at the step 318 and the measured EVENT_TIME in the temporary event buffer 100 (FIG. 2). At the step 328, the control system 34 (FIG. 1) increments the temporary event buffer pointer.

At the step 330, the control system 34 (FIG. 1) stores SAMPLEs, acquired at the step 318 in accordance with the SAMPLING_RATE, in the temporary waveform buffer 112 (FIG. 2). At the step 332, the control system 34 (FIG. 1) increments the temporary waveform buffer pointer in accordance with the SAMPLING_RATE.

At a test 334, the control system 34 (FIG. 1) determines whether EVENT_LIMIT_1 EVENTs have been stored in the temporary event buffer 100 (FIG. 2). If EVENT_LIMIT_1 EVENTs have been stored, the temporary event buffer 100 (FIG. 2) is full, and thus, at a step 336, the control system 34 (FIG. 1) resets the temporary event buffer pointer to the TEMP_BUFFER_START position. At this point, newly acquired EVENTs and measured EVENT_TIMEs will overwrite previously stored data. If EVENT_LIMIT_1 EVENTs have not been stored, the control system 34 (FIG. 1) proceeds to a test 338.

At a test 338, the control system 34 (FIG. 1) determines whether SAMPLE_LIMIT_1 SAMPLEs have been stored in the temporary waveform buffer 112 (FIG. 2). If SAMPLE_LIMIT_1 SAMPLEs have been stored, the temporary waveform buffer 112 (FIG. 2) (FIG. 2) is full, and thus, at a step 340, the control system 34 (FIG. 1) resets the temporary waveform buffer pointer to the WAVEFORM_BUFFER_START position. At this point, newly acquired SAMPLEs will overwrite previously stored data. If SAMPLE_LIMIT_1 SAMPLEs have not been stored, the control system 34 (FIG. 1) proceeds to a test 342.

At the test 342, the control system 34 (FIG. 1) determines whether EVENT_LIMIT_2 EVENTs have been stored in the event snapshot buffer 146 (FIG. 3) since the TRIGGER_CRITERIA_MARK was placed by the control system 34 (FIG. 1) at a step 374. If EVENT_LIMIT_2 EVENTs have been stored, at a step 344, the control system 34 (FIG. 1) sets the CRITERIA_MET_FLAG_1 to "OFF," and places a SNAPSHOT_END marker in the event snapshot buffer 128 (FIG. 3), after the EVENT recorded during the current program cycle, to indicate the start of the next event snapshot. At a step 346, the control system 34 (FIG. 1) increments the SNAPSHOT_COUNTER_1.

At a test 348 the control system 34 (FIG. 1) determines whether SNAPSHOT_COUNTER_1 is greater than EVENT_SNAPSHOT_MAX. If SNAPSHOT_COUNTER_1 is greater, at a test 350, the control system 34 (FIG. 1) determines whether the LIMIT_TO_MEMORY_FLAG is set to "ON." If the LIMIT_TO_MEMORY_FLAG is set to "ON," at a step 352, the control system 34 (FIG. 1) resets the event snapshot pointer to the SNAPSHOT_BUFFER_1_START position. Otherwise, at a step 354, the control system 34 (FIG. 1) sets the SNAPSHOT_1_RECORDING to "OFF." The control system 34 (FIG. 1) then proceeds to a test 356.

At the test 356, the control system 34 (FIG. 1) determines whether SAMPLE_LIMIT_2 SAMPLEs have been stored in the waveform snapshot buffer 140 (FIG. 3) since the TRIGGER_CRITERIA_MARK was placed by the control system 34 (FIG. 1) at a step 378. If SAMPLE_LIMIT_2 SAMPLEs have been stored, at a step 358, the control system 34 (FIG. 1) sets the CRITERIA_MET_FLAG_2 to "OFF," and places a SNAPSHOT_END marker in the waveform snapshot buffer 128 (FIG. 3), after the EVENT recorded during the current program cycle, to indicate the start of the next event snapshot. At a step 360, the control system 34 (FIG. 1) increments the SNAPSHOT_COUNTER_2.

At a test 362 the control system 34 (FIG. 1) determines whether SNAPSHOT_COUNTER_2 is greater than WAVEFORM_SNAPSHOT_MAX. If SNAPSHOT_COUNTER_2 is greater, at a test 364, the control system 34 (FIG. 1) determines whether the LIMIT_TO_MEMORY_FLAG is set to "ON." If the LIMIT_TO_MEMORY_FLAG is set to "ON," at a step 366, the control system 34 (FIG. 1) resets the waveform snapshot pointer to the SNAPSHOT_BUFFER_2_START position. Otherwise, at a step 368, the control system 34 (FIG. 1) sets the SNAPSHOT_2 RECORDING to "OFF." The control system 34 (FIG. 1) then proceeds to the test 306.

If at the test 324, the control system 34 (FIG. 1) determined that one or more of the TRIGGER_CRITERIA have been met, the control system 34 (FIG. 1) proceeds to a step 370. At the step 370, the control system 34 (FIG. 1) sets both CRITERIA_MET_FLAG_1 and CRITERA_MET_FLAG_2 to "ON."

At a step 372, the control system 34 (FIG. 1) transfers the contents of the temporary event buffer 100 (FIG. 2) to the event snapshot buffer 146 (FIG. 3). At the step 374, the control system 34 (FIG. 1) places the TRIGGER_CRITERIA_MARK and the TIME_MARK in the event snapshot buffer 146 (FIG. 3).

At a step 376, the control system 34 (FIG. 1) transfers the contents of the temporary waveform buffer 112 (FIG. 2) to the waveform snapshot buffer 140 (FIG. 3). At the step 378, the control system 34 (FIG. 1) places the TRIGGER_CRITERIA_MARK and the TIME_MARK in the waveform snapshot buffer 140 (FIG. 3).

At the step 380, the control system 34 (FIG. 1) measures the EVENT_TIME from the EVENT acquired during the previous program cycle, and then stores the EVENT acquired at the step 318 and the measured EVENT_TIME in the event snapshot buffer 146 (FIG. 3). At a step 382, the control system 34 (FIG. 1) increments the event snapshot buffer pointer.

At a test 384, the control system 34 (FIG. 1) determines whether the CRITERA_MET_FLAG_2 is "ON." If the CRITERIA_MET_FLAG_2 is "OFF," the control system 34 (FIG. 1) proceeds to the step 330. Otherwise, the control system 34 (FIG. 1) proceeds to a step 386. At the step 386, the control system 34 (FIG. 1) stores SAMPLEs, acquired at the step 318 in accordance with the SAMPLING_RATE, in the waveform snapshot buffer 140 (FIG. 3). At the step 388, the control system 34 (FIG. 1) increments the waveform snapshot buffer pointer in accordance with the SAMPLING_RATE. The control system 34 (FIG. 1) then proceeds to the test 334.

At the step 390 the control system 34 (FIG. 1) measures the EVENT_TIME from the EVENT acquired during the previous program cycle, and then stores the EVENT acquired at the step 318 and the measured EVENT_TIME in the temporary event buffer 100 (FIG. 2). At a step 392, the control system 34 (FIG. 1) increments the temporary event buffer pointer. The control system 34 (FIG. 1) then proceeds to the step 386.

Thus a system and method are provided for recording and storing, in long-term memory and in form of data snapshots, medical data acquired prior to and subsequent to occurrence of cardiac episodes and implantable device functions defined as important by the medical practitioner. One skilled in the art will appreciate that the present invention can be practiced by other than the described embodiments, which are presented for purposes of illustration and not of limitation, and the present invention is limited only by the claims that follow.

We claim:

1. A diagnostic system for use with an implantable medical device, the system comprising:
   sensing means for acquiring medical data from a heart;
   first storage means for temporarily storing the medical data acquired by the sensing means;
   a first selection means for selecting at least one trigger criteria from a plurality of trigger criteria;
   second storage means for storing the at least one programmable trigger criterion;
   first control means for applying the at least one trigger criterion to the medical data stored in the first storage means and for determining whether the at least one trigger criteria has been met; and
   third storage means responsive to the first control means, for storing medical data acquired before and after the first control means determines that at least one trigger criterion has been met.

2. The diagnostic system of claim 1, wherein:
   the medical data comprises at least two cardiac events; and
   the medical data further comprises event time data representative of the time between a current cardiac event and a previous cardiac event.

3. The diagnostic system of claim 2, wherein the medical data comprises at least one waveform.

4. The diagnostic system of claim 3, further comprising:
   a physiological sensor for sensing a physiological parameter of the body; and
   selection means for selecting the physiological sensor for the at least one waveform.

5. The diagnostic system of claim 3, further comprising:
   second control means for defining a predetermined number of samples for the at least one waveform that may be acquired by the sensing means during a single cardiac cycle.

6. The diagnostic system of claim 3, wherein the first storage means comprises:
   fourth storage means for temporarily storing the current cardiac event and also for storing the corresponding event time data; and
   fifth storage means for temporarily storing the at least one waveform.

7. The diagnostic system of claim 6, further comprising:
   second control means for defining a first data limit for the fourth storage means, wherein the first data limit is representative of the maximum number of the at least one cardiac events that may be stored in the fourth storage means; and
   third control means for defining a second data limit for the fifth storage means, wherein the second data limit is representative of a maximum number of samples for the at least one waveform that may be stored in the fifth storage means.

8. The diagnostic system of claim 7, wherein the fourth and the fifth storage means are circular buffers, and wherein:
   after the first data limit is reached the first control means overwrites the at least one cardiac event and the event time data stored in the fourth storage means with a newly acquired at least one cardiac event; and
   after the second data limit is reached the first control means overwrites the at least one waveform stored in the fifth storage means with a newly acquired at least one waveform.

9. The diagnostic system of claim 8, wherein the third storage means further comprises:
   sixth storage means responsive to the first control means, for storing at least one event snapshot, wherein the at least one event snapshot is representative of the at least one cardiac event and of the event time data acquired before and after the first control means determine that the at least one trigger criterion has been met; and
   seventh storage means responsive to the first control means, for storing at least one waveform snapshot, wherein the at least one waveform snapshot is representative of the at least one waveform acquired before and after the first control means determine that the at least one trigger criterion has been met.

10. The diagnostic system of claim 9, further comprising:
    fourth control means for disabling the sixth storage means; and
    eleventh control means for disabling the seventh storage means.

11. The diagnostic system of claim 9, further comprising:
    fourth control means, responsive to the first control means, for transferring the medical data stored in the fourth storage means to the sixth storage means, after the first control means determine that the at least one trigger criterion has been met;
    fifth control means, responsive to the first control means, for transferring the medical data stored in the fifth storage means to the seventh storage means, after the first control means determine that the at least one trigger criterion has been met;
    first recording means, responsive to the first control means, for recording into the sixth and the seventh storage means, after the first control means determine that the at least one trigger criterion has been met, data representative of the at least one trigger criterion which has been met, and data representative of the time and date during which the at least one trigger criterion has been met.

12. The diagnostic system of claim 11, further comprising:
    sixth control means for defining a third data limit for the sixth storage means, wherein the third data limit is representative of the number of the at least one cardiac events that must be stored in the sixth storage means after the recording means record the data representative of the time and date during which the at least one trigger criterion has been met; and
    seventh control means for defining a fourth data limit for the seventh storage means, wherein the fourth data limit is representative of maximum number of samples for the at least one waveform that must be stored in the seventh storage means after the recording means record the data representative of the time and date during which the at least one trigger criterion has been met.

13. The diagnostic system of claim 12, wherein after the recording means record data representative of the time and date during which the at least one trigger criterion has been met, the first control means:
    stores the at least one cardiac event newly acquired by the sensing means, and the event time data in the sixth storage means instead of the fourth storage means until the third data limit is reached; and
    stores the at least one waveform newly acquired by the sensing means in the seventh storage means instead of the fifth storage means until the fourth data limit is reached.

14. The diagnostic system of claim 13, wherein the first control means:
   stores a marker representative of the end of the at least one event snapshot, in the sixth storage means when the third data limit is reached; and
   stores a marker representative of the end of the at least one waveform snapshot, in the seventh storage means when the fourth data limit is reached.

15. The diagnostic system of claim 14, further comprising:
   eighth control means for defining a fifth data limit representative of the maximum number of the at least one event snapshots which may be stored in the sixth storage means; and
   ninth control means for defining a sixth data limit representative of the maximum number of the at least one waveform snapshots which may be stored in the seventh storage means.

16. The diagnostic system of claim 15, further comprising tenth control means for defining whether the sixth and seventh storage means operate as circular buffers, wherein:
   when the sixth storage means is defined as a circular buffer, after the fifth data limit is reached the first control means overwrites the at least one event snapshot stored in the sixth storage means with a newly generated at least one event snapshot, starting with the first at least one event snapshot stored in the sixth storage means; and wherein when the sixth storage means is defined as standard buffer, after the fifth data limit is reached the first control means disables the sixth storage means so that no further event snapshots may be stored; and
   when the seventh storage means is defined as a circular buffer, after the sixth data limit is reached the first control means overwrites the at least one waveform snapshot stored in the seventh storage means with a newly generated at least one waveform snapshot, starting with the first at least one waveform snapshot stored in the seventh storage means; and wherein when the seventh storage means is defined as standard buffer, after the sixth data limit is reached the first control means disables the seventh storage means so that no further waveform snapshots may be stored.

17. A diagnostic method for use with a medical device implanted in a patient, the method comprising the steps of:
   (a) acquiring medical data from a heart;
   (b) temporarily storing the medical data acquired during the acquiring step;
   (c) selecting at least one trigger criterion from a plurality of trigger criteria;
   (d) storing the at least one programmable trigger criteria;
   (e) applying the at least one trigger criteria to the medical data stored during step (b);
   (f) determining whether the at least one trigger criteria has been met; and
   (g) storing medical data acquired before and after the determination at step (e) that at least one trigger criterion has been met.

18. The diagnostic method of claim 17, wherein the medical data comprises at least two cardiac events and event time data representative of the time between each of the at least two cardiac events.

19. The diagnostic method of claim 18, wherein the medical data comprises at least one waveform.

20. The diagnostic method of claim 19, further comprising the step of:
   (h) selecting a physiological sensor as a source for the at least one waveform.

21. The diagnostic method of claim 19, further comprising the step of:
   (h) defining the amount of the at least one waveform that may be acquired at step (a) during a single cardiac cycle.

22. The diagnostic method of claim 19, wherein step (b) further comprises the steps of:
   (h) temporarily storing the at least one cardiac event and the event time data in a first memory location; and
   (i) temporarily storing the at least one waveform in a second memory location.

23. The diagnostic method of claim 22, further comprising the steps of:
   defining a first memory limit for the first memory location, wherein the first memory limit is representative of the maximum number of the at least one cardiac events that may be stored in the first memory location; and
   defining a second memory limit for the second memory location, wherein the second memory limit is representative of the maximum number of samples for the at least one waveform that may be stored in the second memory location.

24. The diagnostic method of claim 23, wherein steps (h) and (i) store the medical data in circular buffers, and further comprises the steps of:
   (j) overwriting the at least one cardiac event and the event time data stored in the first memory location with an at least one cardiac event newly acquired at step (a) after the first memory limit is reached; and
   (k) overwriting the at least one waveform stored in the second memory location with an at least one waveform newly acquired at step (a), after the second memory limit is reached.

25. The diagnostic method of claim 24, wherein step (f) further comprises the steps of:
   (l) storing at least one event snapshot in a third memory location, wherein the at least one event snapshot is representative of the at least one cardiac event and of the event time data acquired before and after the determination at step (e) that the at least one trigger criterion has been met; and
   (m) storing at least one waveform snapshot in a fourth memory location, wherein the at least one waveform snapshot is representative of the at least one waveform acquired before and after the determination at step (e) that the at least one trigger criterion has been met.

26. The diagnostic method of claim 25, further comprising the steps of:
   (z) disabling the third memory location; and
   (aa) disabling the fourth memory location.

27. The diagnostic method of claim 25, further comprising the steps of:
   (n) transferring the contents of the first memory location to the third memory location, after the determination at step (e) that the at least one trigger criterion has been met;
   (o) transferring the contents of the second memory location to the fourth memory location, after the determination at step (e) that the at least one trigger criterion has been met; and
   (p) recording into the third and fourth memory locations, after step (o), data representative of the at least one trigger criterion which has been met, and data representative of the time and date during which the at least one trigger criterion has been met.

28. The diagnostic method of claim 27, further comprising the steps of:
   (q) defining a third memory limit for the third memory location, wherein the third memory limit is representative of the number of the at least one cardiac events that must be stored in the third memory location after step (p); and
   (r) defining a fourth memory limit for the fourth memory location, wherein the fourth memory limit is representative of a maximum number of samples for the at least one waveform that must be stored in the fourth memory location after step (p).

29. The diagnostic method of claim 28, further comprising the steps of:
   (s) storing the at least one cardiac event newly acquired at step (a) and the event time data, in the third memory location instead of the first memory location until the third memory limit is reached; and
   (t) storing the at least one waveform newly acquired at step (a) in the fourth memory location instead of the second memory location until the fourth memory limit is reached.

30. The diagnostic method of claim 29, further comprising the steps of:
   (u) storing a marker representative of the end of the at least one event snapshot, in the third memory location when the third memory limit is reached; and
   (v) storing a marker representative of the end of the at least one waveform snapshot, in the fourth memory location when the fourth memory limit is reached.

31. The diagnostic method of claim 30, further comprising the steps of:
   (w) defining a fifth memory limit representative of the maximum number of the at least one event snapshots which may be stored in the third memory location; and
   (x) defining a sixth memory limit representative of the maximum number of the at least one waveform snapshots which may be stored in the fourth memory location.

32. The diagnostic method of claim 31, further comprising the step of:
   (y) defining whether the third and the fourth memory locations operate as circular buffers or as standard buffers, wherein:
   when the third memory location is defined as a circular buffer, after the fifth memory limit is reached, a newly generated at least one event snapshot overwrites the older at least one event snapshot stored in the third memory location; and wherein when the third memory location is defined as standard buffer, after the fifth memory limit is reached the third memory location is disabled so that no further event snapshots may be stored; and
   when the fourth memory location is defined as a circular buffer, after the sixth memory limit is reached, a newly generated at least one waveform snapshot overwrites the older at least one event snapshot stored in the fourth memory location; and wherein when the fourth memory location is defined as standard buffer, after the sixth memory limit is reached, the fourth memory location is disabled so that no further waveform snapshots may be stored.

33. In an implantable cardiac device, a system for recording and storing intracardiac electrogram waveforms, comprising:
   converting means for acquiring and converting intracardiac electrogram waveforms into digitized intracardiac electrogram waveforms;
   storing means, coupled to the converting means, for temporarily storing a first predetermined number of the digitized intracardiac electrogram waveforms;
   detecting means for detecting when a change in a patient's rhythm has occurred and for producing at least one rhythm-change signal in response thereto; and
   control means, in response to the detecting means, for triggering the storing means to permanently store the first predetermined number of digitized intracardiac electrogram waveforms acquired before the at least one rhythm-change signal was detected, and a second predetermined number of digitized intracardiac electrogram waveforms after the at least one rhythm-change signal was detected.

34. The system as recited in claim 33, further comprising:
   means for programmably defining a high atrial rate threshold; and
   means for detecting when the high atrial rate threshold has been exceeded and producing a high atrial rate signal in response thereto;
   wherein the rhythm-change signal comprises the high atrial rate signal.

35. The system as recited in claim 33, further comprising:
   means for programmably defining a low atrial rate threshold; and
   means for detecting when the low atrial rate threshold has been exceeded and producing a low atrial rate signal in response thereto;
   wherein the rhythm-change signal comprises the low atrial rate signal.

36. The system as recited in claim 33, comprising:
   means for programmably defining a high ventricular rate threshold; and
   means for detecting when the high ventricular rate threshold has been exceeded and producing a high ventricular rate signal in response thereto;
   wherein the rhythm-change signal comprises the low atrial rate signal.

37. The system as recited in claim 33, comprising:
   means for programmably defining a low ventricular rate threshold; and
   means for detecting when the low ventricular rate threshold has been exceeded and producing a low ventricular rate signal in response thereto;
   wherein the rhythm-change signal comprises the low ventricular rate signal.

38. The system as recited in claim 33, comprising:
   means for programmably defining a predetermined number of consecutive premature ventricular contractions (PVCs); and
   means for detecting when the predetermined number has been exceeded and producing a high PVC signal in response thereto;
   wherein the rhythm-change signal comprises the high PVC signal.

39. The system as recited in claim 33, further comprising:
   means for programmably defining a predetermined number of consecutive pacemaker mediated tachycardias (PMTs); and means for detecting when the predetermined number has been exceeded and producing a high PMT signal in response thereto;

wherein the rhythm-change signal comprises the high PMT signal.

40. In an implantable cardiac device, a system for recording and storing intracardiac electrogram waveforms, comprising:

converting means for acquiring and converting intracardiac electrogram waveforms into digitized intracardiac electrogram waveforms;

storing means, coupled to the converting means, for temporarily storing a first predetermined number of the digitized intracardiac electrogram waveforms;

programming means for selectively programming a plurality of functions into the implantable medical device;

detecting means for detecting when a change in at least one of the plurality of functions has occurred and for producing a change-in-function signal in response thereto; and control means, in response to the detecting means, for triggering the storing means to permanently store the first predetermined number of digitized intracardiac electrogram waveforms acquired before the at least one change-in-function signal was detected, and a second predetermined number of digitized intracardiac electrogram waveforms after the at least one change-in-function signal was detected.

41. The system as recited in claim 40, wherein:

the control means includes means for selectively operating the implantable device in one of a plurality of modes of operation, the plurality of modes of operation being selectable by the programming means;

the detecting means includes means for detecting a change in at least one of the plurality of modes of operation and for producing a change-in-mode signal in response thereto; and the at least one change-in-function signal comprises the change-in-mode signal.

42. In an implantable cardiac device, a system for recording and storing intracardiac diagnostic data, comprising:

converting means for acquiring a plurality of intracardiac diagnostic data, including intracardiac electrogram waveforms, and converting the data into digitized signals;

storing means, coupled to the converting means, for temporarily storing a first predetermined number of the digitized signals;

detecting means for detecting when a change has occurred in one of the plurality of intracardiac diagnostic data, and for producing a trigger signal in response thereto; and control means, in response to the detecting means, for triggering the storing means to permanently store the first predetermined number of digitized signals acquired before the trigger signal was detected, and a second predetermined number of digitized signals after the trigger signal was detected.

* * * * *